(12) United States Patent
Southard et al.

(10) Patent No.: US 7,067,702 B2
(45) Date of Patent: Jun. 27, 2006

(54) PROCESS FOR PREPARING VINYL SUBSTITUTED BETA-DIKETONES

(75) Inventors: Glen E. Southard, Park City, UT (US); George M. Murray, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/127,897

(22) Filed: May 12, 2005

(65) Prior Publication Data

US 2006/0069288 A1  Mar. 30, 2006

Related U.S. Application Data

(60) Provisional application No. 60/574,124, filed on May 25, 2004.

(51) Int. Cl.
*C07C 45/00* (2006.01)
*C07F 9/00* (2006.01)

(52) U.S. Cl. .................. 568/312; 568/316; 568/317; 568/348; 568/349; 568/394; 568/395; 556/41

(58) Field of Classification Search .................. None
See application file for complete search history.

(56) References Cited

U.S. PATENT DOCUMENTS

| 3,004,932 A * | 10/1961 | Despic et al. ............... 521/26 |
| 6,548,684 B1 * | 4/2003 | Indolese et al. ............. 556/14 |
| 6,867,310 B1 * | 3/2005 | Buchwald et al. ........... 549/453 |

OTHER PUBLICATIONS

Southard et al. Synthesis of Vinyl-Substituted B-Diketones for Polymerization Metal Complexes.□□Journal of Organic Chemistry, 2005, vol. 70, p 9036-9039.*

* cited by examiner

*Primary Examiner*—Sikarl A. Witherspoon
(74) *Attorney, Agent, or Firm*—Francis A. Cooch (57) ABSTRACT

A process for preparing vinyl substituted beta-diketones includes reacting a halogen-containing beta-diketone with an olefin in a reaction zone under Heck coupling reaction conditions in the presence of a catalyst, a base, and an organic phosphine to provide a vinyl substituted beta-diketone product.

19 Claims, 3 Drawing Sheets

PROCESS FOR PREPARING VINYL SUBSTITUTED BETA-DIKETONES

CROSS-REFERENCE TO RELATED APPLICATIONS

This application claims the benefit of prior filed co-pending U.S. application No. 60/574,124, filed on May 25, 2004, the contents of which are incorporated by reference herein.

STATEMENT OF GOVERNMENT INTEREST

This invention was made with Government support under Contract No. F08650-03-C-D012 awarded by the U.S. Army. The Government has certain rights in the invention.

BACKGROUND OF THE INVENTION

1. Field of the Invention

The present invention generally relates to a process for preparing vinyl substituted beta-diketones for use in molecular imprinting.

2. Description of the Related Art

A number of organophosphorus compounds are used as pesticides and nerve agents. For example, organophosphorus based pesticides, including paraoxon, parathion and diazinon are widely used in the agriculture industry and the resultant environmental pollution is well documented. Because of their toxicity and relatively high solubility in water, organophosphorus based pesticides pose a clear threat to drinking water and aquatic life. It is therefore necessary to monitor the levels of these materials in industrial waste water, agricultural runoff, and other environments to determine compliance with federal and state regulations and other safety guidelines, as well as efficiency of wastewater treatments.

In addition, organophosphorus based nerve gases, including tabun and the organo-fluorophosphorus compounds sarin and soman, are of particular concern as chemical weapons which can be used on battlefields or by terrorists in civilian populated areas. Concerns over the use of these chemicals, as well as leakages from aging stockpiles prompt the development of easily used portable devices which can provide real time monitoring capabilities for such compounds.

Chemical sensors must fulfill two goals: (1) the development of a specific chemical recognition element that allows a molecule, or class of molecule, to be identified, and (2) a means of signal transduction in which the presence of the molecule causes a measurable change in a physical property of the material. Although these goals are not always separable, the successful design of chemical sensors requires that both be satisfied.

Most transduction approaches are based on optical, resistive, surface acoustic wave, or capacitive measurements. These well-developed methods dominate largely because of their ease of operation, sensitivity, and cost. The chemical recognition elements in these detectors, however, lag far behind. Indeed, most reports on chemical sensors suggest that many other devices could be fabricated if only suitable chemical recognition units were available. The missing element is a general approach to chemical recognition that allows the rational design and assembly of materials in a stable and reusable form. The present invention solves this problem based on the fabrication of molecularly imprinted polymers (MIPs).

Figure 1:
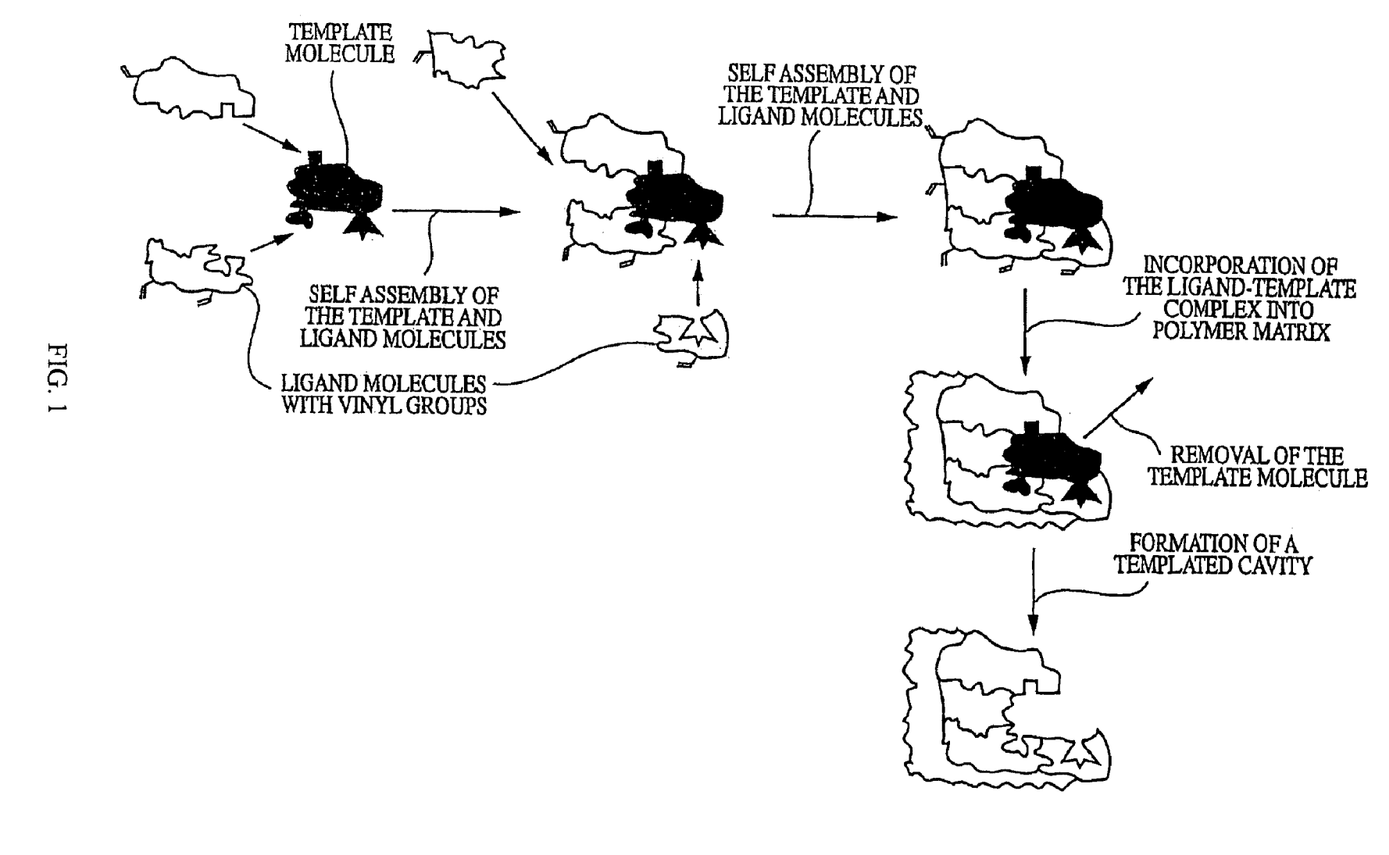
FIG. 1 is a schematic flow chart illustrating a known method of molecularly imprinting to obtain a molecularly imprinted polymer.

An MIP is generally described as a plastic cast or mold of the molecule of interest, where recognition is based on shape, much like a lock and key. MIPs are made by adding the molecule of interest to a solution of binding molecules that can be chemically incorporated into a polymer. See FIG. 1. These binders usually have an affinity for the target and form a complex.

The interactions that hold these complexes together include $\pi$—$\pi$ interactions, hydrogen bonding, metal-ligand binding, and even covalent bond formation, but they must be reversible. The binder must also have a chemical functionality that allows it to be irreversibly bound to polymers. Vinyl groups are a common functional group used to prepare many polymers, e.g., polyethylene, polystyrene, polyvinylalcohol, and polyvinylchloride. The target-binder complex is dissolved in excess matrix monomer (for example, styrene) and possibly other additives such as a cross-linker and porogens (solvents).

In a typical sensor fabrication, a solid plastic mass, consisting of the matrix and binder, is obtained which is chemically bound to the polymer/cross-linker matrix and the target molecule. Removal of the target is possible since it is reversibly bound to the binder. The cavity it leaves behind is permanently shaped like the target.

Sensors for organophosphorus compounds can be based on the luminescence of a lanthanide ion. See, for example, U.S. Pat. No. 6,749,811 B2, which is herein incorporated by reference. The process is enhanced when the lanthanide has sensitizing ligands. If the ligands can be polymerized a MIP sensor can be made.

Vinyl substituted beta-diketones are useful for forming a complex with a lanthanide ion. This complex can be reacted with a target analyte to produce an adduct which is subsequently incorporated into a polymeric matrix. The analyte can then be removed to provide the molecularly imprinted polymer (MIP).

It would be advantageous to have an efficient and economical process for preparing vinyl substituted beta-diketone.

SUMMARY OF THE INVENTION

A process is provided herein for making vinyl substituted beta-diketones. In one embodiment, the process comprises reacting a halogen-containing beta-diketone with an olefin in a reaction zone under Heck coupling reaction conditions in the presence of a catalyst, a base, and an organic phosphine to provide a vinyl substituted beta-diketone product.

BRIEF DESCRIPTION OF THE DRAWINGS

Various embodiments are described below with reference to the drawings wherein.

DETAILED DESCRIPTION OF THE PREFERRED EMBODIMENTS

The process of the present invention advantageously employs Heck reaction coupling to prepare vinyl beta-diketones. Recent work in Heck chemistry has reduced thermal demands needed for olefin substitution, thereby mitigating concerns about autopolymerization or hydrogenation of the vinyl group.

In the Heck reaction, an olefin containing a least one hydrogen attached to at least one of the double bonded carbons is reacted with an organic halide in the presence of a catalyst and base to produce a hydrogen halide and an olefin with the hydrogen substituted with the organic group of the halide.

As applied to the process of the invention, the Heck coupling reaction can be employed to produce vinyl substituted beta-diketones and divinyl beta-diketones.

Referring now to reaction (I) below a beta diketone [A] is reacted with olefin [B] to produce vinyl substituted beta-diketone [C] as follows:

wherein

X is a halogen or halogen-containing moiety, e.g., Cl, Br, I, triflate ($OSO_2CF_3$), etc., $R^1$ is an unsaturated aliphatic, aromatic, alkylaryl or arylalkyl group of from 2 to about 20 carbon atoms, or a heterocyclic group;

$R^2$ can be the same or different and is hydrogen or a hydrocarbon group having from 1 to about 12 carbon atoms.

$R^3$ is a straight or branched chain alkyl group with or without substituents, or an aryl, alkaryl or arylalkyl group with or without substituents.

$R^4$, $R^5$ and $R^6$ can be the same or different and are selected from hydrogen and straight chain or branched alkyl groups of from 1 to about 12 carbon atoms. In a preferred embodiment, the olefin is ethylene.

Preferably, X is a halogen, e.g., bromine, $R^1$ is an aryl group with or without alkyl substituents or a heterocyclic group, such as a sulfur-containing heterocyclic moiety, $R^2$ is hydrogen, $R^3$ is —$CF^3$, or aryl, and $R^4$, $R^5$ and $R^6$ are hydrogen.

In another embodiment, the $R^3$ group includes a substituent X which is substituted with the olefinic compound (B) so as to produce a divinyl substituted beta-diketone.

Generally, the Heck coupling reaction is carried out in the presence of a catalyst, base, and an organic phosphine.

A catalyst for use herein can be a palladium catalyst such as, for example, dipalladium tris (dibenzylidenelacetone) ("PdDBA"), palladium chloride bis triphenyl phosphine ($Pd(PPh_3)_2Cl_2$), palladium tetra triphenylphosphine ($Pd(PPh_3)_4$), palladium acetate ($Pd(OC(O)CH_3)_2$), palladium chloride ($PdCl_2$), and the like.

Useful bases include, but are not limited to, amine bases, alkali metal carbonates, alkali metal hydroxides, alkali metal acetates and the like and mixtures thereof. Suitable amine bases include, but are not limited to, trialkyl amines such as triethylamine and tripropylamine, cycloalkyl amines such as methyl dicyclohexylamine, and the like. Suitable alkali metal carbonates include, but are not limited to, potassium carbonate, sodium carbonate, and the like. Suitable alkali metal acetates include, but are not limited to, potassium acetate, sodium acetate and the like. Suitable alkali metal hydroxides include, but are not limited to, potassium hydroxides, sodium hydroxides and the like.

Useful phosphorus containing organic compound include, but are not limited to, triphenyl phosphine, tri t-butyl phosphine, tris(p-tolyl)phoshine, tricyclohexyl phosphine, tris(p-chloro phenyl)phosphine, tris(p-fluoro phenyl)phosphine, tris(p-methoxy phenyl)phosphine, tributyl phosphine, tris (isopropyl)phosphine, tri-o-tolyl phosphine and the like and mixtures thereof.

If desired, the reaction can be conducted in water or a solvent. Useful solvents include, but are not limited to, polar solvents such as dimethylformamide, 1,4-dioxane, methanol, ethanol or acetonitrile, or non-polar solvents such as benzene, toluene, and the like and mixtures thereof.

The Heck coupling reaction is preferably conducted at 20° C. to 160° C., more preferably at about 20° C. to 30° C. and under an inert atmosphere with the injection of olefin at an elevated pressure (preferably 250 psi to 350 psi). The reaction is allowed to proceed, preferably with stirring for a sufficient period of time, e.g., a time period ranging from about 12 to about 48 hours. Upon completion of the reaction, the contents of the reactor are preferably added to water and ether.

The vinyl substituted beta-diketone can then be purified. For example, the vinyl substituted beta-diketone can be purified by acidifying the aqueous phase, extracting with ether, rinsing with sodium chloride solution, separating and dewatering the organic phase by, e.g., adding a drying agent such as magnesium sulfate or calcium chloride, and then removing the solvent by, for example, vacuum.

The extracted vinyl substituted beta diketone ligand can then be reacted with a lanthanide to form a complex. The term lanthanide as used herein refers to elements 57 to 71 of the Periodic Table of the Elements including lanthanum (La), cerium (Ce), praseodymium (Pr), neodymium (Nd), promethium (Pm) samarium (Sm), europium (Eu), gadolinium (Gd), terbium (Tb), dysprosium (Dy), holmium (Ho), erbium (Er), thulium (Tm), ytterbium (Yb) and lutetium (Lu). Europium is preferred. In general, the complex can be formed by reacting three moles of ligand or mixed ligands with about one mole of lanthanide halide such as $EuC_3$. This reaction is generally carried out in an aqueous solution in the presence of an alkali metal hydroxide (e.g., NaOH) or an amine, e.g., ammonia or a trialkylamine such as triethylamine, which reacts with the vinyl substituted beta-diketone to form an alkali metal (i.e., sodium) beta-diketonate. The vinyl substituted beta diketone ligand is preferably first dissolved in a solvent such as tetrahydrofuran. The reaction is terminated by the addition of an alcohol (e.g. methanol, ethanol, etc.).

When lanthanide ions are chelated with appropriate ligands, a significant enhancement of the luminescence intensity is obtained. The chelated lanthanide complexes of the present invention provide a sensitive means of analysis with low limits of detection when incorporated in a MIP. For example, lanthanide ions can form complexes with various organic molecules such as β-diketones, polyaminopolycarboxylic acids (EDTA and the like), (poly)pyridines and calixarenes. Moreover, ligands containing organic chromophores possessing suitable photophysical properties provide highly luminescent lanthanide complexes. See, e.g., Jenkins, A., et al., "Ultratrace Determination of Selected Lanthanides by Luminescence Enhancement," *Anal. Chem.*, 68(17):2974–2980 (1996) (the entire disclosure of which is incorporated herein by reference). With a careful selection of complexing ligands, metal complexes can be synthesized by mixing stoichiometric amounts of a lanthanide metal salt and the complexing ligand(s) in an aqueous solution and evaporating to near dryness. Water or alcohol/water mixtures of the lanthanide metal and ligand in stoichiometric ratios, evaporated to dryness, are preferred to obtain near quantitative yield of the desired complex compound. In one embodiment, to make complexes that contain target anions, mixed ligand complexes that have a one-to-one stoichiometric ratio of target anion to complex can be employed. This can be accomplished by synthesizing lanthanide metal ion complexes with the proper coordination number of tightly binding ligands such that a single target analyte could bind by replacing a very weakly bound substituent.

The europium (III) β-diketone complexes can be formed by reaction of the sodium β-diketonate with europium chloride hexahydrate in acetone/water solution. The stability of the complex and luminescent efficiency of the europium reporter is directly related to the β-diketone used to generate the reporting complex. Additionally, the hydrolytic stability of the europium (III) β-diketone complexes also depends upon the number of vinyl groups as well as the placement of the vinyl groups on the aromatic ring. For example, 4,4'-DVDBM would only form europium (III) β-diketone complexes under rigorously dry reaction conditions. Addition of any water to the reaction would immediately decompose the complex. The other β-diketones gave europium complex of varying hydrolytic stability with 3-VDBM being the most stable. Presumably the added steric demands of the vinyl groups decreased the stability of the europium (III) β-diketone complexes.

The complex can then be combined with a target analyte such as an organophosphorus compound to form an adduct.

The reaction of the lanthanide complex with the target analyte (e.g., an organophosphorus compound) to form an adduct can be carried out by first dissolving the target analyte in a suitable solvent and then reacting it with the complex at a temperature of from ambient to about 100° C. for a sufficient period of time (e.g., about 1 to about 10 hours). If desired, the reaction can be conducted under an inert atmosphere (e.g., in nitrogen, argon, etc.). The resulting adduct can then be separated by known techniques. A preferred target organophosphorus analyte is a compound having the formula $(R^7)(R^8)(R^9)P=O$, wherein $R^7$, $R^8$ and $R^9$ can be the same or different and are individually selected from inorganic or organic groups, provided that at least one group is organic. Exemplary groups include, but are not limited to, those selected from H, —OH, halogen (e.g., F, Cl, Br, I), nitrile (—CN), nitro ($NO_2$), and organic groups such as, for example, substituted or unsubstituted, saturated or unsaturated aliphatic or aromatic groups with or without heteroatoms such as, for example, alkyl, cycloalkyl, alkenyl, alkoxy, and the like. The organophosphorus compound is exemplified herein with the use of dimethyl hydrogen phosphate (DMHP) having the formula $(CH_3O)_2P(O)H$, or pinacolyl methyl phosphonate ("PMP") having the formula:

$$((CH_3)_3-C-(CH_3)CH-O-)(CH_3-)(HO-)P=O.$$

The resulting adduct can then be dissolved in a matrix monomer which can then be polymerized to form a solid mass containing the adduct bound by chemical linkages to the polymerized matrix.

A wide variety of monomers may be used for synthesizing the MIP in accordance with the principles of the present invention. Suitable non-limiting examples of monomers that can be used for preparing a MIP of the present invention include methylmethacrylate, other alkyl methacrylates, alkylacrylates, allyl or aryl acrylates and methacrylates, cyanoacrylate, styrene, -methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)—acryloxy-,'-dimethyl-g-butyrolactone; N-acryloxy succinimide-acryloxytris(hydroxymethyl) aminomethane; N-acryloly chloride; N-acryloyl pyrrolidinone; N-acryloyl-tris(hydroxymethyl)amino methane; 2-amino ethyl methacrylate; N-(3-aminopropyl)methacrylamide; (o, m, or p)-amino-styrene; t-amyl methacrylate; 2-(1-aziridinyl)ethyl methacrylate; 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; -bromostyrene; p-bromostyrene; bromotrifluoro ethylene; (±)-3-buten-2-ol; 1,3-butadiene; 1,3-butadiene-1,4-dicarboxylic acid 3-butenal diethyl acetal; 1-butene; 3-buten-2-ol; 3-butenyl chloroformate; 2-butylacrolein; -t-butylacrylamide; butyl acrylate; butyl methacrylate; (o,m,p)-bromostyrene; t-butyl acrylate; (R)-carvone; (S)-carvone; (–)-carvyl acetate; cis 3-chloroacrylic acid; 2-chloroacrylonitrile; 2-chloroethyl vinyl ether; 2-chloromethyl-3-trimethylsilyl-1-propene; 3-chloro-1-butene; 3-chloro-2-chloromethyl-1-propene; 3-chloro-2-methyl propene; 2,2-bis(4-chlorophenyl)-1,1-dichloroethylene; 3-chloro-1-phenyl-1-propene; m-chlorostyrene; o-chlorostyrene; p-chlorostyrene; 1-cyanovinyl acetate; 1-cyclopropyl-1-(trimethylsiloxy)ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2,2-difluoroethylene; 1,1-dichloropropene; 2,6-difluorostyrene; dihydrocarveol; (±)-dihydrocarvone; (–)-dihydrocarvyl acetate; 3,3-dimethylacrylaldehyde; N,N'-dimethylacrylamide; 3,3-dimethylacrylic acid; 3,3-dimethylacryloyl chloride; 2,3-dimethyl-1-butene; 3,3-dimethyl-1-butene; 2-dimethyl aminoethyl methacrylate; 1-(3-butenyl)-4-vinylbenzene; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstyrene; 3,4-dimethylstryene; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl-2-(hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o-fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4-diol; 1,4-hexadiene; 1,5-hexadien-3-ol; 1,3,5-hexatriene; 5-hexen-1,2-diol; 5-hexen-1-ol; hydroxypropyl acrylate; 3-hydroxy-3,7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; (±)-: linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide;

methacrylic acid; methacrylic anhydride; methacrylonitrile; methacryloyl chloride; 2-(methacryloyloxy)ethyl acetoacetate; (3-methacryloxypropyl) trimethoxy silane; 2-(methacryloxy)ethyl trimethyl ammonium methylsulfate; 2-methoxy propene (isopropenyl methyl ether); methyl-2-(bromomethyl)acrylate; 5-methyl-5-hexen-2-one; methyl methacrylate; N,N'-methylene bisacrylamide; 2-methylene glutaronitrile; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2-methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; -methyl styrene; t--methylstyrene; t--methylstyrene; 3-methylstyrene; methyl vinyl ether; methyl vinyl ketone; methyl-2-vinyloxirane; 4-methylstyrene; methyl vinyl sulfone; 4-methyl-5-vinylthiazole; myrcene; t--nitrostyrene; 3-nitrostyrene; 1-nonadecene; 1,8-nonadiene; 1-octadecene; 1,7-octadiene; 7-octene-1,2-diol; 1-octene; 1-octen-3-ol; 1-pentadecene; 1-pentene; 1-penten-3-ol; t-2,4-pentenoic acid; 1,3-pentadiene; 1,4-pentadiene; 1,4-pentadien-3-ol; 4-penten-1-ol; 4-penten-2-ol; 4-phenyl-1-butene; phenyl vinyl sulfide; phenyl vinyl sulfonate; 2-propene-1-sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; trans 3-chloroacrylic acid; 2-trifluoromethyl propene; 2-(trifluoromethyl)propenoic acid; 2,4,4'-trimethyl-1-pentene; 3,5-bis(trifluoromethyl) styrene; 2,3-bis(trimethylsiloxy)-1,3-butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4-vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; 1-vinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbornene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfonic acid sodium salt; o-vinyl toluene; p-vinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenyphosphonium bromide (triphenyl vinyl phosphonium bromide); vinyl tris-(2-methoxyethoxy) silane; vinyl 2-valerate and the like.

Acrylate-terminated or otherwise unsaturated urethanes, carbonates, and epoxies can also be used in the MIP. An example of an unsaturated carbonate is allyl diglycol carbonate. Unsaturated epoxies include, but are not limited to, glycidyl acrylate, glycidyl methacrylate, allyl glycidyl ether, and 1,2-epoxy-3-allyl propane.

Crosslinking agents that impart rigidity or structural integrity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malonate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2-isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, divinyl benzene; 1,3-divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12,17-tetramethyl-21H,23H-propionic acid disodium salt; 3,9-divinyl-2,4,8,10-tetraoraspiro[5,5]undecane; divinyl tin dichloride and the like.

The polymerization can be carried out neat or in a porogen, or solvent, which can be any solvent suitable for the purposes described herein. Suitable solvents include, but are not limited to, toluene, xylene, methoxyethanol, and the like and mixtures.

Any suitable conditions effective to polymerize the monomers of the present invention to produce an MIP without dissociating the chelated lanthanide-analyte complex may be used. The monomers of the present invention may be polymerized by free radical polymerization, and the like.

Any UV or thermal free radical initiator known to those skilled in the art can be used in the preferred free radical polymerization. Examples of UV and thermal initiators include benzoyl peroxide, acetyl peroxide, lauryl peroxide, azobisisobutyronitrile (AIBN), t-butyl peracetate, cumyl peroxide, t-butyl peroxide; t-butyl hydroperoxide, bis(isopropyl)peroxy-dicarbonate, benzoin methyl ether, 2,2'-azobis(2,4-dimethyl-valeronitrile), tertiarybutyl peroctoate, phthalic peroxide, diethoxyacetophenone, and tertiarybutyl peroxypivalate, diethoxyacetophenone, 1-hydroxycyclohexyl phenyl ketone, 2,2-dimethoxy-2-phenylacetophenone, and phenothiazine, diisopropylxanthogen disulfide, 2,2'-azobis-(2-amidinopropane); 2,2'-azobisisobutyronitrile-; 4,4'-azobis-(4-cyanovaleric acid); 1,1'-azobis-(cyclohexanecarbonitrile)-; 2,2'-azobis-(2,4-dimethylvaleronitrile); and the like and mixtures thereof.

The choice of monomer and cross-linking agent will be dictated by the chemical (hydrophilicity, chemical stability, degree of cross-linking, ability to graft to other surfaces, interactions with other molecules, etc.) and physical (porosity, morphology, mechanical stability, etc.) properties desired for the polymer. The amounts of chelated lanthanide-analyte complex, monomer and crosslinking agents should be chosen to provide a crosslinked polymer exhibiting the desired structural integrity, porosity and hydrophilicity. The amounts can vary broadly, depending on the specific nature/ reactivities of the chelated lanthanide-analyte complex, monomer and crosslinking agent chosen as well as the specific application and environment in which the polymer will ultimately be employed. The relative amounts of each reactant can be varied to achieve desired concentrations of chelated lanthanide-analyte complexes in the polymer support structure. Typically, the amount of chelated lanthanide-analyte complex will be on the order of about 0.01 mmol to about 100 mmol percent of monomer. The solvent, temperature, and means of polymerization can be varied in order to obtain polymeric materials of optimal physical or chemical features, for example, porosity, stability, and hydrophilicity. The solvent will also be chosen based on its ability to solubilize all the various components of the reaction mixture.

Polymerizations are generally conducted in bulk solution by the free-radical method. For bulk polymerization, typically the amount of chelated lanthanide-analyte complex will be on the order of about 0.01 mmol to about 100 mmol percent of monomer, about 90 to about 99 mol percent monomer and about 1.0 to about 10 mol percent cross-linker, and about 1 mol percent of a free radical initiator are dissolved in an aqueous/organic two-phase solvent. The reaction mixture is placed under an inert atmosphere and heated to a temperature of from about 50° C. to about 100° C. for about 24 to about 72 hours. As one skilled in the art will readily appreciate, styrenic polymerizations can be thermally initiated. It is particularly advantageous to prepare a block copolymer employing two or more of the foregoing monomers.

When polymerization is complete, the crosslinked polymer may be washed, cryogenically ground to a uniformly fine powder, and/or extensively eluted with nonpolar solvents to remove any unreacted lanthanide-analyte complex. The steps of grinding and/or freezing in liquid nitrogen may be used to maximize surface area and allow for access by the various reagents and samples. Freezing allows the polymer to become brittle enough to be ground and prevents distortions of the polymer by the heat of friction.

Removal of the target molecule leaves a macroporous polymer with complementary molecular cavities which include lanthanide complexes that have specific binding affinity for the target molecule. The target molecule comprising, for example, an organophosphorus compound, may be dissociated from the metal ion complex binding site within the polymer in a manner that does not adversely affect the imprinted cavity. In embodiments wherein the target molecule is covalently bound to the functional monomer, any appropriate method can be used to cleave the covalent bond, although the covalent bond formed should preferably be cleaved under conditions suitable to release the imprint molecule after the MIP is formed, without adversely affecting the selective binding characteristics of the MIP. To accomplish this, acetone, isopropanol, methanol or other suitable organic solvent may be used to swell the resultant polymers, allowing greater access to the coordinated metal ions because imprinted resins have a relatively low amount of functionalization and are primarily nonionic matrices. The covalent bond that is cleaved to release the imprint molecule can optionally provide an additional polar or ionic site for design and imprinting of the imprint molecule. In preferred embodiments wherein the target analyte is associated with the lanthanide in a non-covalent manner, the non-covalently bound analyte is simply leached or washed out after polymerization. For example, for organophosphorus compound imprinted resins, subsequent to the removal of unreacted monomer, a 1 N aqueous acidic solution may be mixed into the acetone washes, with increasing aqueous acidic phase in each sequential wash, to remove the imprint molecule from the cavities. In certain preferred embodiments, an acidic solvent having a pH of about 4.5 or less is used. In certain other preferred embodiments, resin mass action is used to replace a target anion with an easily exchangeable anion by immersing the polymer in a solution containing the easily exchangeable anion at a suitable pH.

The polymer of the invention can be prepared in a wide variety of forms ranging from powders to beads to macro structures such as films, plates, rods, membranes or coatings or other materials which can be used to detect the presence of the target analyte in the environment.

As can be appreciated by the skilled artisan, the preferred synthetic schemes and embodiments described above and in the Examples below are not intended to comprise a comprehensive list of all means by which the polymer described and claimed herein may be synthesized. It will be understood that the specified materials and conditions are important in practicing the invention but that unspecified materials and conditions are not excluded so long as they do not prevent the benefits of the invention from being realized. Other suitable methods and starting materials will be evident to those having skill in the art. Additionally, the various synthetic steps described throughout this written description may be performed in an alternate sequence or order to obtain the present invention.

EXAMPLES

The invention is illustrated below by Examples 1–8. Comparative Examples A and B are presented for comparison purposes and do not illustrate the invention. Reference is made below to specific diketones. To facilitate the description, the following acronyms are employed:

| | |
|---|---|
| VBA | Vinylbenzoylacetone |
| 4,4'-DVDBM | 4,4'-Divinyldibenzoyl methane |
| 4-VDBM | 4-Vinyldibenzoyl methane |
| 3-VDBM | 3-Vinyldibenzoyl methane |
| 3,5-DVDBM | 3,5-Divinyldibenzoyl methane |
| VTTFA | Vinylthenoyltrifluoro acetone |
| VNTFA | Vinylnaphthoyltrifluroacetone |

The beta-diketones employed in these Examples were synthesized mostly by condensation reactions to build a halogen substituted beta-diketone. 4-Bromobenzoylacetone was synthesized by the condensation of 4-bromomethylbenzoate with acetone under basic conditions. The dibenzoylmethanes required a multistep synthesis as yields from condensing halogenated methylbenzoates with acetophenone or a halogenated derivative were very low. Hence, the base catalyzed condensation of the appropriate acetophenone and the appropriate benzaldehyde gave the corresponding benzalacetophenone, which were subsequently reacted with elemental bromine followed by bromide elimination with sodium methoxide. Hydrolysis of the methoxide intermediate gave the halogenated beta-diketone in good yield.

The trifluoromethyl and halogen substituted β-diketones, 4-bromo napthoyltrifluoroacetone and 5-bromothenoyltrifluoroacetone, were synthesized by condensation of acetylbromoarene with ethyltrifluoroacetate under basic conditions in ether. It was found that potassium tert-butoxide gave better results for 4-bromo napthoyltrifluoroacetone, while sodium methoxide was an excellent base for generating 5-bromothenoyltrifluoroacetone.

The vinyl substituted beta-diketones were found to be readily synthesized by utilizing Heck coupling technique. The benzene derivatives of the halogenated beta-diketones were found to give moderate to good yields of the vinyl beta-diketones in all cases. Care must be taken to avoid extended reaction times as hydrogenation of the vinyl moiety predominates. However, the electron rich halogen substituted thiophene and nathphalene beta-diketones require milder reaction temperature. Fortunately, recent work in Heck chemistry has dramatically reduced the thermal demands needed for olefin substitution. Accordingly, VTTFA and VNTFA were synthesized in moderate yield without hydrogenation of the vinyl group or autopolymerzation concerns.

The europium (III) beta-diketone complexes were formed by reaction of the sodium beta-diketonate with europium chloride hexahydrate in acetone/water solution. The stability of the reporting complex and luminescent efficiency of the europium reporter is directly related to the beta-diketone used to generate the reporting complex. The hydrolytic stability of the europium (III) beta-diketone complexes also depends upon the number of vinyl groups as well as the placement of the vinyl groups on the aromatic ring. 4,4'-DVDBM would only form europium (III) beta-diketone complexes under rigorously dry reaction conditions. Addition of any water to the reaction would immediately decompose the complex. The other beta-diketones gave europium complexes of varying hydrolytic stability with 3-VDBM being the most stable.

NMR was performed on either a Bruker AC-200 MHz spectrometer or an Anaszai 90 MHz spectrometer; FT-IR was performed on a Bomems MB-122; GC/MS was performed on a Shimadzu QP 5050A. 4-Vinyl-methylbenzoate and 4-bromomethyl-methylbenzoate were synthesized by a modified Shea method (K. I. Shea; G. J. Stoddard *Macromolecules* 1991, 24, 1207–1209). All chemicals were provided by Sigma-Aldrich unless otherwise stated, and were used without further purification. The Heck coupling was performed with either a Parr Instruments HC 677 100 mL reactor or a PPI LC series 300 mL reactor.

Figure 2:
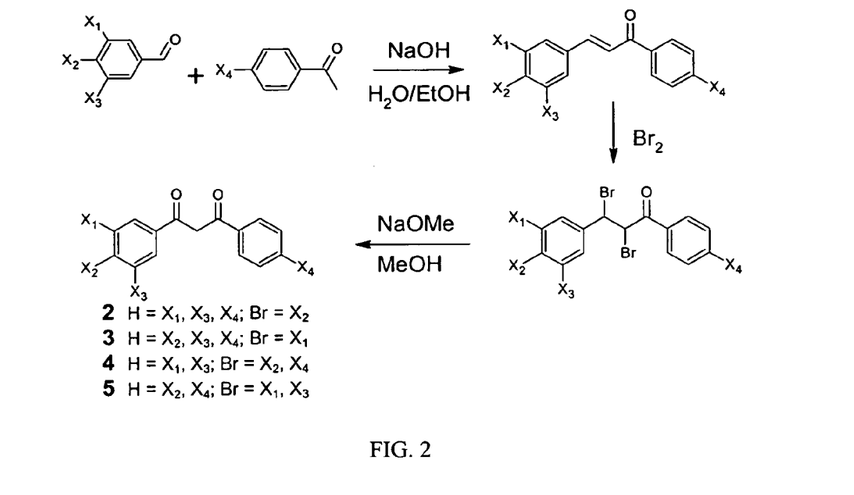
FIG. 2 is a schematic flow chart illustrating the reaction schemes for the Comparative Examples A and B.
Figure 3:
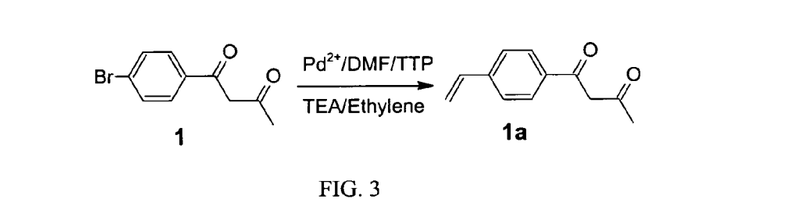
FIGS. 3–5 are a schematic flow chart illustrating the reaction schemes for the Examples 1–8.
Figure 4:
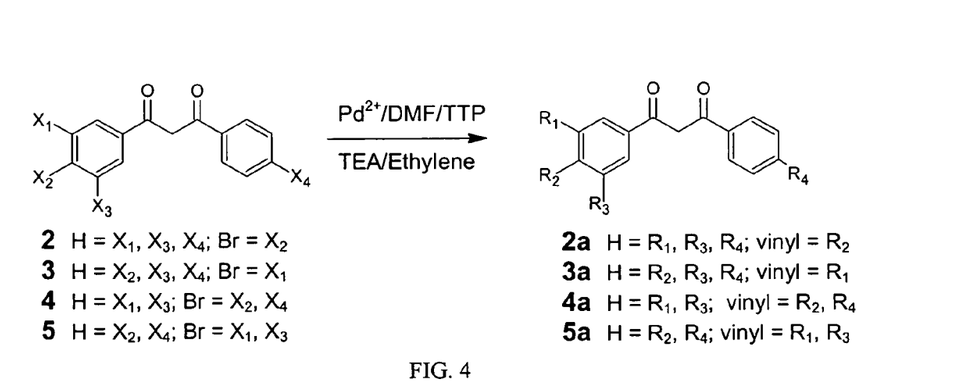
Figure 5:
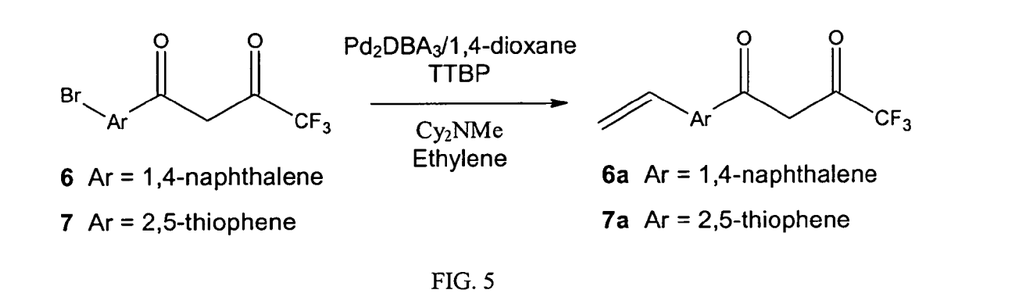

4-Vinylmethylbenzoate and 4-bromomethylmethylbenzoate (procedure a) were synthesized by a modified Shea method. The 1-acetyl-4-bromonaphthalene was synthesized by standard Friedel-Crafts acylation of 1-bromonaphthalene with acetyl chloride and aluminum chloride. All chemicals were provided by Sigma-Aldrich unless otherwise stated, and were used without further purification. The Heck coupling was performed with either a Parr Instruments HC 677 100 mL reactor or a PPI LC series 300 mL reactor. The reaction scheme for Comparative Examples A and B is illustrated in FIG. 2. The reaction scheme for Examples 1–8 is illustrated in FIGS. 3–5.

Comparative Example A

Step 1

Synthesis of 4-vinylbenzoylacetone: Dry tetrahydrofuran (10 mL), sodium hydride (1.7 g, 70 mmol), and 4-vinyl-methylbenzoate (8.0 g, 49 mmol) were placed in a flame dried, three-necked, round bottomed flask equipped with a reflux condenser, nitrogen inlet, addition funnel and magnetic stir bar. Dry tetrahydrofuran (5 mL) and dry acetone (4.3 mL, 59 mmol) was added dropwise to the refluxing mixture containing 4-vinyl-methylbenzoate. The mixture was allowed to reflux for an additional two hours before allowed to cool to room temperature. Concentrated hydrochloric acid (1 mL) was added, the mixture was diluted with ether (50 mL) and water (50 mL), and the mixture was made acidic by a further addition of concentrated hydrochloric acid. The aqueous phase was rinsed with ether (2×50 mL), and the combined organic phase was washed with 1 M sodium hydroxide (3×50 mL). The combined alkali phases were rinsed with pentane. The alkali solution was acidified with concentrated hydrochloric acid, which formed a precipitate. The precipitate was removed from the aqueous phase by rinsing with ether (2×50 mL), and the combined organic phases were rinsed with saturated sodium bicarbonate solution (3×50 mL). The organic phase was dried with magnesium sulfate for 16 hours before filtration and isolation of the yellow material (4 g, 43% yield). $^1$H-NMR (200 MHz, 25° C., CDCl$_3$): δ 16.12 (s, 1H), 7.83 (d, 2H), 7.45 (d, 2H), 6.70 (dd, 1H), 6.17 (s, 1H), 5.82 (d, 1H), 5.35 (d, 1H), 2.20 (s, 3H).

Comparative Example B

Synthesis of 4-vinyldibenzoylmethane: Dry tetrahydrofuran (10 mL), sodium hydride (1.3 g, 54 mmol), and 4-vinyl methylbenzoate (6.0 g, 37 mmol) were placed in a flame dried, three-necked, round bottomed flask equipped with a reflux condenser, nitrogen inlet, addition funnel and magnetic stir bar. Dry tetrahydrofuran (5 mL) and dry acetone (5.4 mL, 45 mmol) was added dropwise to the refluxing mixture containing 4-vinyl-methylbenzoate. The mixture was allowed to reflux for an additional twenty-four hours before allowed to cool to room temperature. Concentrated hydrochloric acid (1 mL) was added, the mixture was diluted with ether (50 mL) and water (50 mL), and the mixture was made acidic by a further addition of concentrated hydrochloric acid. The aqueous phase was rinsed with ether (2×50 mL), and the combined organic phase was washed with 1 M sodium hydroxide (3×50 mL). The combined alkali phases were rinsed with pentane. The alkali solution was acidified with concentrated hydrochloric acid, which formed a precipitate. The precipitate was removed from the aqueous phase by rinsing with ether (2×50 mL), and the combined organic phases were rinsed with saturated sodium bicarbonate solution (3×50 mL). The organic phase was dried with magnesium sulfate for 16 hours before filtration and isolation of the yellow material (0.6 g, 6.5% yield). $^1$H-NMR (200 MHz, 25° C., CDCl$_3$): δ 16.20 (s, 1H), 8.00 (d, 4H), 7.55 (d, 4H), 6.80 (dd, 2H), 6.70 (s, 1H), 5.90 (d, 2H), 5.40 (d, 2H).

Example 1

Synthesis of 4-vinylbenzoylacetone: Dimethyl formamide (30 mL), palladium acetate (0.022 g, 0.1 mmol), tri-o-tolyl phosphine (0.060 g, 0.2 mmol), triethylamine (9.1 g, 90 mmol), 4-bromobenzoylacetone (2.41 g, 10 mmol) were added to a 100 mL Parr high pressure reactor with an inner glass liner. The solution was degassed with nitrogen for 10 minutes before the reactor was cooled to −196° C. and ethylene (1.7 g, 61 mmol) was condensed for 20 minutes. The reactor was allowed to warm to room temperature before heating to 100° C. in an oil bath. The pressure was bled off until 300 psi was achieved and the reaction was allowed to proceed for 12 hours. The reaction vessel was cooled to room temperature, the extra pressure bled, and the contents dissolved in water (50 mL) and ether (50 mL). The aqueous phase was made acidic by addition of concentrated hydrochloric acid followed by extraction with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with chloroform as eluent. The first band collected resulted in a yellow powder (1.03 g, 55% yield) upon solvent removal. $^1$H-NMR (200 MHz, 25° C., CDCl$_3$): δ 16.12 (s, 1H), 7.83 (d, 2H), 7.45 (d, 2H), 6.70 (dd, 1H), 6.17 (s, 1H), 5.82 (d, 1H), 5.35 (d, 1H), 2.20 (s, 3H).

Example 2

Step 1

Synthesis of 4,4'-dibromobenzalacetophenone: Sodium hydroxide (1.8 g, 45 mmol) and 4-bromoacetophenone (7.12 g, 36 mmol) were dissolved in water (18 mL) and ethanol (50 mL). 4-Bromo benzaldehyde (6.62 g, 36 mmol) dissolved in ethanol (20 mL) was added dropwise to the acetophenone solution. A slurry quickly formed, which was allowed to stir overnight. The slurry was filtered, was with water until the filtrate was neutral to pH paper, and dried at 100° C. for 12 hours. A light tan solid was obtained (12.8 g, 97% yield).

Step 2

Synthesis of 1,3-bis(4-bromophenyl)-2,3-dibromopropanone: 4,4'-Dibromobenzalacetophenone (12.8 g, 35 mmol) was dissolved in refluxing chloroform (300 mL) and bromine (5.6 g, 35 mmol) was added dropwise. A precipitate immediately formed. The solution was cooled to room temperature, the precipitate was isolated by filtration, and was washed with cool chloroform (100 mL). The light pink precipitate (17.38 g, 95% yield) was air dried.

Step 3

Synthesis of 4,4'-dibromodibenzoylmethane: Sodium metal (2.0 g, 85.5 mmol) was reacted with excess methanol (100 mL) to give sodium methoxide in methanol. 1,3-Bis(4-bromophenyl)-2,3-dibromopropanone (18.0 g, 34.2 mmol) was suspended in methanol (50 mL) and the methanolic sodium methoxide solution was added dropwise. The mixture soon cleared and was heated to reflux for 1 hour. Concentrated hydrochloric acid (5 mL) was added, the solution was allowed to reflux for an additional 5 minutes before water (50 mL), and the solution was allowed to cool to room temperature. Filtration of the resulting precipitate gave pale yellow crystals (11.9 g, 96% yield), which were allowed to air dry.

Step 4

Synthesis of 4,4'-divinyldibenzoylmethane: Dimethyl formamide (30 mL), palladium acetate (0.022 g, 0.1 mmol), tri-o-tolyl phosphine (0.060 g, 0.2 mmol), triethylamine (9.1 g, 90 mmol), 4,4'-dibromodibenzoylmethane (3.82 g, 10 mmol) were added to a 100 mL Parr high pressure reactor with an inner glass liner. The solution was degassed with nitrogen for 10 minutes before the reactor was cooled to −196° C. and ethylene (1.7 g, 61 mmol) was condensed for 20 minutes. The reactor was allowed to warm to room temperature before heating to 100° C. in an oil bath. The pressure was bled off until 300 psi was achieved and the reaction was allowed to proceed for 12 hours. The reaction vessel was cooled to room temperature, the extra pressure bled, and the contents dissolved in water (50 mL) and ether (50 mL). The aqueous phase was made acidic by addition of concentrated hydrochloric acid followed by extraction with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with chloroform as eluent. The first band collected resulted in a yellow powder (1.70 g, 62% yield) upon solvent removal. $^1$H-NMR (200 MHz, 25° C., CDCl$_3$): δ 16.20 (s, 1H), 8.00 (d, 4H), 7.55 (d, 4H), 6.80 (dd, 2H), 6.70 (s, 1H), 5.90 (d, 2H), 5.40 (d, 2H).

Example 3

Step 1

Synthesis of 4-iodo-4'-bromobenzalacetophenone: Sodium hydroxide (5.5 g, 138 mmol) and 4-iodoacetophenone (25.0 g, 102 mmol) were dissolved in water (50 mL) and ethanol (80 mL). 4-Bromo benzaldehyde (18.8 g, 102 mmol) dissolved in ethanol (40 mL) was added dropwise to the acetophenone solution. A slurry quickly formed, which was allowed to stir overnight. The slurry was filtered, was with water until the filtrate was neutral to pH paper, and dried at 100° C. for 12 hours. A light tan solid was obtained (21.1 g, 50% yield).

Step 2

Synthesis of 1-(4-iodophenyl)-3-(4-bromophenyl)-2,3-dibromopropanone: 4-Iodo-4'-bromobenzalacetophenone (5.0 g, 12 mmol) was dissolved in refluxing chloroform (200 mL) and bromine (1.93 g, 12 mmol) was added dropwise. The solution was concentrated to 50 mL, was cooled to room temperature, the resulting precipitate was isolated by filtration, and was washed with cool chloroform (100 mL). The light pink precipitate (5.43 g, 78% yield) was allowed to air dry.

Step 3

Synthesis of 4-bromo-4'-iododibenzoylmethane: Sodium metal (0.58 g, 35 mmol) was reacted with excess methanol (15 mL) to give sodium methoxide in methanol. 1-(4-Iodophenyl)-3-(4-bromophenyl)-2,3-dibromopropanone (5.43 g, 10 mmol) was suspended in methanol (10 mL) and the methanolic sodium methoxide solution was added dropwise. The mixture soon cleared and was heated to reflux for 1 hour. Concentrated hydrochloric acid (1 mL) was added, the solution was allowed to reflux for an additional 5 minutes before water (20 mL), and the solution was allowed to cool to room temperature. Filtration of the resulting precipitate gave pale yellow crystals (2.41 g, 56% yield), which were allowed to air dry.

Step 4

Synthesis of 4-bromobenzalacetophenone: Sodium hydroxide (1.88 g, 47 mmol) and 4-bromoacetophenone (7.47 g, 37.5 mmol) were dissolved in water (15 mL) and ethanol (50 mL). Benzaldehyde (4.00 g, 37.5 mmol) dissolved in ethanol (20 mL) was added dropwise to the acetophenone solution. A slurry quickly formed, which was allowed to stir overnight. The slurry was filtered, was with water until the filtrate was neutral to pH paper, and dried at 100° C. for 12 hours. A light tan solid was obtained (10.0 g, 93% yield).

Step 5

Synthesis of 1-(4-bromophenyl)-3-phenyl-2,3-dibromopropanone: 4-Bromobenzalacetophenone (12.0 g, 42 mmol) was dissolved in chloroform (150 mL) and bromine (6.7 g, 42 mmol) was added dropwise. A precipitate immediately formed, the solution was stirred for an additional two hours, the precipitate was isolated by filtration, and was washed with cool chloroform (100 mL). The light pink precipitate (13.25 g, 85% yield) was air dried.

Step 6

Synthesis of 4-bromodibenzoylmethane: Sodium metal (1.71 g, 74.1 mmol) was reacted with excess methanol (80 mL) to give sodium methoxide in methanol. 1-(4-Bromophenyl)-3-phenyl-2,3-dibromopropanone (13.25 g, 29.6 mmol) was suspended in methanol (50 mL) and the methanolic sodium methoxide solution was added dropwise. The mixture soon cleared and was heated to reflux for 1 hour. Concentrated hydrochloric acid (3 mL) was added, the solution was allowed to reflux for an additional 5 minutes before water (50 mL), and the solution was allowed to cool to room temperature. Filtration of the resulting precipitate gave pale yellow crystals, which were allowed to air dry, recrystallized twice from hexanes to give an off-white powder (4 g, 45% yield). $^1$H-NMR (200 MHz, 25° C., CDCl$_3$): δ 16.81 (s, 1H), 8.01 (d, 2H), 7.84 (d, 2H), 7.61 (m, 3H), 7.46 (d, 2H), 6.81 (s, H), 5.40 (d, 2 H). (found/calc for $C_{15}H_{11}BrO_2$) 59.59 (59.42), H 3.93 (3.82).

Step 7

Synthesis of 4-vinyldibenzoylmethane: Dimethyl formamide (30 mL), palladium acetate (0.022 g, 0.1 mmol), tri-o-tolyl phosphine (0.060 g, 0.2 mmol), triethylamine (9.1 g, 90 mmol), 4-bromodibenzoylmethane (3.03 g, 10 mmol) were added to a 100 mL Parr high pressure reactor with an inner glass liner. The solution was degassed with nitrogen for 10 minutes before the reactor was cooled to –196° C. and ethylene (1.7 g, 61 mmol) was condensed for 20 minutes. The reactor was allowed to warm to room temperature before heating to 100° C. in an oil bath. The pressure was bled off until 300 psi was achieved and the reaction was allowed to proceed for 12 hours. The reaction vessel was cooled to room temperature, the extra pressure bled, and the contents dissolved in water (50 mL) and ether (50 mL). The aqueous phase was made acidic by addition of concentrated hydrochloric acid followed by extraction with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with chloroform as eluent. The first band collected resulted in a yellow powder (2.2 g, 88% yield) upon solvent removal. $^1$H-NMR (200 MHz, 25° C., CDCl$_3$): δ 16.91 (s, 1H), 7.98 (m, 4H), 7.50 (m, 5H), 6.96 (s, 1H), 6.86 (dd, 2H), 5.90 (d, 2H), 5.40 (d, 2H). Anal.: (found/calc for $C_{17}H_{14}O_2$) 81.71 (81.58), H 5.65 (5.59).

Example 4

Step 1

Synthesis of 3,5-dibromobenzalacetophenone: Sodium hydroxide (1.00 g, 25 mmol) and acetophenone (2.37 g, 19.7 mmol) were dissolved in water (10 mL) and ethanol (10 mL). 4-Bromobenzaldehyde (5.21 g, 19.7 mmol) dissolved in ethanol (30 mL) was added dropwise to the acetophenone solution. A slurry quickly formed, which was allowed to two additional hours. The slurry was filtered, was with water until the filtrate was neutral to pH paper, and dried at 100° C. for 12 hours. Light yellow crystals were obtained (4.1 g, 57% yield).

Step 2

Synthesis of 1-(3,5-dibromophenyl)-3-phenyl-2,3-dibromopropanone: 3,5-Dibromobenzalacetophenone (4.1 g, 11.2 mmol) was dissolved in chloroform (20 mL) and bromine (1.8 g, 11.2 mmol) was added dropwise. A precipitate immediately formed, the solution was stirred for an additional two hours, the precipitate was isolated by filtration, and was recrystallized from hexanes (100 mL) giving off-white crytals (4.0 g, 68% yield).

Step 3

Synthesis of 3-5-dibromodibenzoylmethane: Sodium metal (2.04 g, 88.6 mmol) was reacted with excess methanol (30 mL) to give sodium methoxide in methanol. 1-(3,5-Dibromophenyl)-3-phenyl-2,3-dibromopropanone (17.7 g, 33.7 mmol) was suspended in methanol (50 mL) and the methanolic sodium methoxide solution was added dropwise. The mixture soon cleared and was heated to reflux for 1 hour. Concentrated hydrochloric acid (3 mL) was added, the solution was allowed to reflux for an additional 5 minutes before water (50 mL), and the solution was allowed to cool to room temperature. Filtration of the resulting precipitate gave pale yellow crystals, which were allowed to air dry, recrystallized twice from 1:1 ethanol/acetone to give an off-white powder (8.48 g, 66% yield). $^1$H-NMR (200 MHz, 25° C., CDCl$_3$): δ 16.81 (s, 1H), 8.01 (d, 2H), 7.84 (d, 2H), 7.61 (m, 3H), 7.46 (d, 2H), 6.81 (s, H), 5.40 (d, 2H).

Step 4

Synthesis of 3,5-divinyldibenzoylmethane: Dimethyl formamide (30 mL), palladium acetate (0.022 g, 0.1 mmol), tri-o-tolyl phosphine (0.060 g, 0.2 mmol), triethylamine (9.1 g, 90 mmol), 3,5-dibromodibenzoylmethane (2.0 g, 5.2 mmol) were added to a 100 mL Parr high pressure reactor with an inner glass liner. The solution was degassed with nitrogen for 10 minutes before the reactor was cooled to –196° C. and ethylene (1.7 g, 61 mmol) was condensed for 20 minutes. The reactor was allowed to warm to room temperature before heating to 100° C. in an oil bath. The pressure was bled off until 300 psi was achieved and the reaction was allowed to proceed for 12 hours. The reaction vessel was cooled to room temperature, the extra pressure bled, and the contents dissolved in water (50 mL) and ether (50 mL). The aqueous phase was made acidic by addition of concentrated hydrochloric acid followed by extraction with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with chloroform as eluent. The first band collected resulted in a yellow powder (0.82 g, 56% yield) upon solvent removal. $^1$H-NMR (200 MHz, 25° C., CDCl$_3$): δ 16.88 (s, 1H), 7.98–7.50 (m, 8H), 6.82 (s, 1H), 6.77 (dd, 2H), 5.92 (d, 2 H), 5.40 (d, 2H). Anal.: (found/calc for $C_{19}H_{16}O_2$) 82.62 (82.58), H 5.91 (5.79).

Example 5

Step 1

Synthesis of 3-bromobenzalacetophenone: Sodium hydroxide (12.00 g, 300 mmol) and acetophenone (24 g, 200 mmol) were dissolved in water (90 mL) and methanol (300 mL). 3-Bromobenzaldehyde (37 g, 200 mmol) dissolved in ethanol (50 mL) was added dropwise to the acetophenone solution. A slurry quickly formed, which was allowed to two additional hours. The slurry was filtered, was with water until the filtrate was neutral to pH paper, and dried at 80° C. for 12 hours. Light yellow crystals were obtained (43.4 g, 75.6% yield).

Step 2

Synthesis of 1-(3-bromophenyl)-3-phenyl-2,3-dibromopropanone: 3-Bromobenzalacetophenone (43.4 g, 151 mmol) was dissolved in chloroform (200 mL) and bromine (24.2 g, 151 mmol) was added dropwise. The solution was stirred for an additional hours before removing the chloroform to give a pink solid (67.6 g 100% yield). The crude material was used without further purification. (found/calc for $C_{15}H_{11}Br_3O$) 39.88 (40.31), H 2.68 (2.46).

Step 3

Synthesis of 3-bromodibenzoylmethane: Sodium metal (8.7 g, 380 mmol) was reacted with excess methanol (120 mL) to give sodium methoxide in methanol. 1-(3-Bromophenyl)-3-phenyl-2,3-dibromopropanone (67.6 g, 151 mmol) was suspended in methanol (100 mL) and the methanolic sodium methoxide solution was added dropwise. The mixture soon cleared and was heated to reflux for 1 hour. Concentrated hydrochloric acid (10 mL) was added, the solution was allowed to reflux for an additional 5 minutes before water (50 mL), and the solution was allowed to cool to room temperature whereupon an oil separated from solution. The oil was dissolved in refluxing hexanes and cooled to room temperature, where white needles crystallized (22.6 g, 50% yield). $^1$H-NMR (200 MHz, 25° C., CDCl$_3$): δ 16.81 (s, 1H), 8.01 (d, 2H), 7.84 (d, 2H), 7.61 (m, 3H), 7.46 (d, 2H), 6.81 (s, H), 5.40 (d, 2H). Anal.: (found/calc for $C_{15}H_{11}BrO_2$) 59.37 (59.42), H 3.66 (3.82).

Step 4

Synthesis of 3-vinyldibenzoylmethane: Dimethyl formamide (90 mL), palladium acetate (0.066 g, 0.3 mmol), tri-o-tolyl phosphine (0.180 g, 0.6 mmol), triethylamine (27.3 g, 270 mmol), 3-bromodibenzoylmethane (9.09 g, 30 mmol) were added to a PPI LC series 300 mL reactor with an inner glass liner. The solution was degassed with argon for 10 minutes before ethylene (1.7 g, 61 mmol, 300 psi) was added. The reactor was to 100° C. and the reaction was allowed to proceed for 12 hours. The reaction vessel was cooled to room temperature, the extra pressure bled, and the contents dissolved in water (50 mL) and ether (50 mL). The aqueous phase was made acidic by addition of concentrated hydrochloric acid followed by extraction with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with chloroform as eluent. The first band collected resulted in a yellow powder (2.2 g, 88% yield) upon solvent removal. $^1$H-NMR (90 MHz, 25° C., CDCl$_3$): δ 16.91 (s, 1H), 8.00 (m, 4H), 7.62 (m, 5H), 6.84 (s, 1H), 6.81 (dd, 2H), 5.92 (d, 2H), 5.40 (d, 2H). Anal.: (found/calc for $C_{17}H_{14}O_2$) 81.58 (81.60), H 5.06 (5.63).

Example 6

Step 1

Synthesis of 4-bromo-1-naphthoyltrifluoroacetone: Ethyltrifluoroacetate (6.91 g, 49 mmol) was added dropwise to an ether (10 mL) solution containing sodium t-butoxide (6.7 g, 52 mmol), which formed a slurry. The 4-bromo-1-acetyl-naphthalene (12.2 g, 49 mmol) was added to the slurry in several large additions and the solution was allowed to stir for 18 hours. The solution was diluted with additional ether (50 mL) and was washed with 1 M hydrochloric acid (2×50 mL). The ethereal solution was dried over magnesium sulfate, filtered and the solvent removed. The 4-bromonapthoyltrifluoroacetone could was separated from the unreacted 4-bromo-1-acetylnaphthalene by forming the copper bis(diketonate) from a methanolic solution of the raw β-diketone and cupric chloride. The first band collected resulted in a yellow powder (9.8 g, 58% yield) upon solvent removal. $^1$H-NMR (90 MHz, 25° C., CDCl$_3$): δ 14.15 (s, 1H), 8.40 (m, 2H), 7.67 (m, 4H), 6.47 (s, 1H). Anal.: (found/calc for $C_{17}H_{14}O_2$) 81.71 (81.58), H 5.65 (5.59).

Step 2

Synthesis of 1-vinylnaphthoyltrifluoroacetone: 1,4-Dioxane (40 mL), tri-t-butylphosphine (0.182 g, 0.9 mmol), and methyldicyclohexylamine (19.5 g, 100 mmol) were placed into a Schlenk flask and transferred by syringe to a PPI LC series 300 mL reactor containing dipalladium tris(dibenzylidenelacetone) (0.420 g, 0.45 mmol) and 4-bromonapthoyltrifluoroacetone (10.4 g, 30 mmol) under an argon atmosphere. The reactor was charged to 300 psi with ethylene and the reaction was allowed to stir for 48 hours at room temperature. Upon completion of the reaction the contents taken up in water (50 mL) and ether (50 mL), the aqueous phase acidified by addition of concentrated hydrochloric acid, and extracted with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with 10% ether in chloroform as eluent. The solvent was removed to give a light brown oil (9.08 g, 99% yield). $^1$H-NMR (90 MHz, 25° C., CDCl$_3$): δ 14.49 (s, 1H), 8.48 (m, 1H), 8.06 (m, 1H), 7.58 (m, 4H), 7.45 (dd, 1H), 6.45 (s, 1H), 5.91 (dd, 1H), 5.62 (dd, 1H). Anal.: (found/calc for $C_{17}H_{14}O_2$) 65.75 (81.58), H 3.79 (5.59).

Example 7

Step 1

Synthesis of 5-bromothenoyltrifluoroacetone: Ethyltrifluoroacetate (6.91 g, 49 mmol) was added dropwise to an ether (10 mL) solution containing sodium methoxide (2.8 g, 52 mmol) which formed a slurry. The 5-bromo-2-acetylthiophene (10 g, 49 mmol) was added to the slurry in several large additions and the solution was allowed to stir for 18 hours. The solution was diluted with additional ether (50 mL) and was washed with 1 M hydrochloric acid (2×50 mL). The ethereal solution was dried over magnesium sulfate, filtered and the solvent removed. The 5-bromothenoyltrifluoroacetone could was separated from the unreacted 2-bromothiophene by vacuum distillation (150° C., 2 torr) or be isolated by forming the copper bis(diketonate) from a methanolic solution of the raw β-diketone and cupric chloride. The first band collected resulted in a yellow powder (7.4 g, 50% yield) upon solvent removal. $^1$H-NMR (90 MHz, 25° C., CDCl$_3$): δ 16.91 (s, 1H), 8.00 (m, 4H), 7.62 (m, 5H), 6.84 (s, 1H), 6.81 (dd, 2H), 5.92 (d, 2H), 5.40 (d, 2H). Anal.: (found/calc for $C_{17}H_{14}O_2$) 81.71 (81.58), H 5.65 (5.59).

Step 2

Synthesis of 5-vinylthenoyltrifluoroacetone: 1,4-Dioxane (40 mL), tri-t-butylphosphine (0.182 g, 0.9 mmol), and methyldicyclohexylamine (19.5 g, 100 mmol) were placed into a Schlenk flask and transferred by syringe to a PPI LC series 300 mL reactor containing dipalladium tris(dibenzylidenelacetone) (0.420 g, 0.45 mmol) and 5-bromothenoyltrifluoroacetone (9 g, 30 mmol) The reactor was charged to 300 psi with ethylene and the reaction was allowed to stir for 48 hours at room temperature. Upon completion of the reaction the contents taken up in water (50 mL) and ether (50 mL), the aqueous phase acidified by addition of concentrated hydrochloric acid, and extracted with ether (2×50 mL). The combined organic phase was rinsed with saturated sodium chloride solution, and the organic phase was dried over magnesium sulfate overnight. The solution was filtered, the solvent was removed by vacuum, and the residue dissolved in chloroform (3 mL). The product was isolated by column chromatography from silica gel (Selecto, mesh size 63-200) with 10% ether in chloroform as eluent. The solvent was removed to give a light green solid (2.4 g, 32% yield). The solid was reacted with cupric chloride dehydrate in methanol, precipitated by addition of water, and recrystallized from THF/hexanes to give $(VTTFA)_2Cu \cdot 1.5THF$. $^1$H-NMR (90 MHz, 25° C., $CDCl_3$): δ 14.25 (s, 1H), 7.63 (d, 1H), 7.12 (d, 1H), 6.94 (dd, 1H), 6.36 (s, 1H), 5.86 (s, 1H). Anal.: (found/calc for $C_{26}H_{24}CuF_6O_{5.5}S_2$) 81.71 (81.58), H 5.65 (5.59).

Example 8

Two analytes of interest were investigated, DMHP and PMP. It was found that PMP decomposed complexes not having the trifluoromethane moiety to tris(pinacolylmethylphosphinato) europium and free β-diketone. DMHP was found to be relatively unreactive towards complexes not containing ligands with trifluoromethane moieties. The VTTFA and VNTFA europium (III) complexes readily formed adducts with both PMP and DMHP when dissolved in chloroform.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A process for preparing vinyl substituted beta-diketones comprising:
    reacting a halogen-containing beta-diketone with an olefin in a reaction zone under Heck coupling reaction conditions in the presence of a catalyst, a base, and an organic phosphine to provide a vinyl substituted beta-diketone product.

2. The process of claim 1, wherein the halogen-containing beta-diketone is of the formula:

$X—CR^1—C(O)—CR^2_2—C(O)—R^3$ wherein
    X is a halogen or halogen-containing moiety;
    $R^1$ is a saturated or unsaturated aliphatic, aromatic, alkylaryl, arylalkyl group of from 2 to 20 carbon atoms or a heterocyclic group;
    $R^2$ can be the same or different and is a hydrogen or hydrocarbon group having from 1 to 12 carbon atoms, and $R^3$ is a straight or branched chain alkyl group with or without substituents, or an aryl, alkaryl or arylalkyl group with or without substituents.

3. The process of claim 2, wherein X is selected from the group consisting of I, Br, Cl and $OSO_2CF_3$.

4. The process of claim 2, wherein the halogen-containing beta-diketone is selected from the group consisting of 4-bromobenzoyl acetone, 4,4'-dibromodibenzoyl methane, 4-bromodibenzoyl methane, 3,5-dibromodibenzoyl methane, 3-bromodibenzoyl methane, bromothenoyltrifluoro acetone and bromonaphthoyltrifluoroacetone.

5. The process of claim 1, wherein the olefin contains from 2 to 20 carbon atoms.

6. The process of claim 1 wherein the catalyst is selected from the group consisting of dipalladium tris(dibenzylidenelacetone), palladium chloride bistriphenylphosphine, palladium tetra triphenylphosphine, palladium acetate and palladium chloride.

7. The process of claim 1 wherein the base is an amine selected from the group consisting of triethylamine, tripropylamine and methyl dicyclohexylamine.

8. The process of claim 1 wherein the base is an alkali metal carbonate, alkali metal acetate or alkali metal hydroxide.

9. The process of claim 1 wherein the organic phosphine is selected from the group consisting of triphenyl phosphine, tri t-butyl phosphine, tris(p-tolyl)phoshine, tricyclohexyl phosphine, tris(p-chloro phenyl)phosphine, tris(p-fluoro phenyl)phosphine, tris(p-methoxy phenyl)phosphine, tributyl phosphine, tris(isopropyl)phosphine and tri-o-tolyl phosphine.

10. The process of claim 1 wherein the vinyl substituted beta-diketone product is a divinyl substituted beta-diketone.

11. The process of claim 10 wherein the reaction is carried out in water or a solvent selected from the group consisting of dimethylformamide, 1,4-dioxane, methanol, ethanol, acetonitrile, benzene and toluene.

12. The process of claim 1 wherein the Heck coupling reaction conditions include a temperature of from about 20° C. to about 160° C. and a reaction time of from about 12 hours to about 48 hours.

13. The process of claim 1 wherein the olefin is injected into the reaction zone at a pressure of from about 250 psi to about 350 psi.

14. The process of claim 1 further comprising complexing the vinyl substituted beta-diketone product with a lanthanide to provide a lanthanide vinyl substituted beta-diketone complex.

15. The process of claim 14 wherein the lanthanide is europium and a europium (III) beta-diketone complex is formed by the reaction of europium halide and the vinyl substituted beta-diketone product in the presence of an alkali metal hydroxide.

16. The process of claim 14 further comprising forming an adduct including the lanthanide vinyl substituted beta diketone complex and a target analyte comprising the steps of:
    dissolving the target analyte in a solvent; and
    reacting the dissolved target analyte with the lanthanide vinyl substituted beta diketone complex.

17. The process of claim 16 wherein the target analyte is an organophorous compound having the formula:

$R^7R^8R^9P=O$ wherein $R^7$, $R^8$ and $R^9$ can be the same or different and are individually selected from the group consisting of hydrogen, halogen, nitrile, nitro, substituted or unsubstituted aliphatic or aromatic groups with or without heteroatoms, with the proviso that at least one of $R^7$, $R^8$ and $R^9$ is organic.

18. The process of claim 16 further comprising copolymerizing the adduct with a matrix monomer to form a solid plastic mass.

19. The process of claim 18 further comprising removing the target analyte from the solid plastic mass by solvent extraction to form a molecularly imprinted polymer.

* * * * *